United States Patent
Palazzini et al.

(10) Patent No.: US 7,259,152 B2
(45) Date of Patent: Aug. 21, 2007

(54) METHODS AND COMPOSITIONS USING SULODEXIDE FOR THE TREATMENT OF DIABETIC NEPHROPATHY

(75) Inventors: Ernesto Palazzini, Bologna (IT); Giovanni Gambaro, Scorze (Venezia) (IT)

(73) Assignee: Alfa Wasserman, Inc., West Caldwell, NJ (US)

( * ) Notice: Subject to any disclaimer, the term of this patent is extended or adjusted under 35 U.S.C. 154(b) by 0 days.

(21) Appl. No.: 09/873,234

(22) Filed: Jun. 4, 2001

(65) Prior Publication Data

US 2002/0065233 A1    May 30, 2002

Related U.S. Application Data

(60) Provisional application No. 60/209,907, filed on Jun. 7, 2000.

(51) Int. Cl.
A01N 43/04 (2006.01)
A61K 31/715 (2006.01)
C07H 1/00 (2006.01)

(52) U.S. Cl. .............. 514/54; 536/18.7; 536/21; 536/55; 536/55.1; 536/55.2; 536/123.1; 536/123.12; 514/57; 514/62

(58) Field of Classification Search .......... 514/54, 514/57, 62; 536/18.7, 21, 55, 55.1, 55.2, 536/123.1, 123.12
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes | |
| 3,916,899 A | 11/1975 | Theeuwes | |
| 3,936,351 A | 2/1976 | Bianchini | |
| 4,008,719 A | 2/1977 | Theeuwes | |
| 4,945,086 A | 7/1990 | Benitz et al. | |
| 5,010,063 A | 4/1991 | Piani et al. | |
| 5,059,595 A | 10/1991 | Le Grazie | |
| 5,073,543 A | 12/1991 | Marshall et al. | |
| 5,073,643 A | 12/1991 | Marshall et al. | |
| 5,104,860 A | 4/1992 | Piani et al. | |
| 5,120,548 A | 6/1992 | McClelland | |
| 5,236,910 A | 8/1993 | Egidio | |
| 5,252,339 A * | 10/1993 | Cristofori | ............ 424/479 |
| 5,354,556 A | 10/1994 | Sparks | |
| 5,380,716 A | 1/1995 | Conrad et al. | |
| 5,405,949 A | 4/1995 | Ungarelli et al. | |
| 5,410,039 A | 4/1995 | Ungarelli et al. | |
| 5,430,132 A | 7/1995 | Silvano et al. | |
| 5,430,133 A | 7/1995 | Piani et al. | |
| 5,464,942 A | 11/1995 | Sakurai et al. | |
| 5,470,965 A | 11/1995 | Baldacci et al. | |
| 5,496,807 A * | 3/1996 | Marchi et al. | ............ 514/52 |
| 5,543,403 A | 8/1996 | Petitou et al. | |
| 5,585,361 A | 12/1996 | Burns et al. | |
| 5,591,767 A | 1/1997 | Mohr | |
| 5,639,476 A | 6/1997 | Oshlack et al. | |
| 5,672,334 A | 9/1997 | Ranney | |
| 5,674,533 A | 10/1997 | Santus et al. | |
| 5,674,633 A | 10/1997 | Santus et al. | |
| 5,686,432 A * | 11/1997 | Baggio et al. | ............ 514/56 |
| 5,733,566 A | 3/1998 | Lewis | |
| 5,861,383 A | 1/1999 | Cardin et al. | ............ 514/56 |
| 6,080,732 A * | 6/2000 | Palazzini et al. | ............ 514/56 |
| 6,399,078 B1 | 6/2002 | Devico et al. | ............ 424/278.1 |

FOREIGN PATENT DOCUMENTS

| | | |
|---|---|---|
| EP | 0 485 748 A2 | 5/1992 |
| EP | 0 497 162 | 8/1992 |
| EP | 0 624 374 | 11/1994 |
| EP | 0 710 483 | 5/1996 |
| EP | 0513513 | 8/1996 |
| EP | 0 950 413 | 10/1999 |
| EP | 1 016 410 | 7/2000 |

OTHER PUBLICATIONS

Ansel H.C., Introduction to Pharmaceutical Dosage Forms, Lea and Febiger, Philadelphia, PA (1985) (Table of Contents).

Baggio B. et al., "Urinary Glycosaminoglycans, Sialic Acid and Lysosomal Enzymes Increase in Nonalbuminuric Diabetic Patients", Nephron 43:187-190 (1986).

Callas D.D. et al., "Comparative Pharmacologic Pharmacologic Profile of a Glycosaminoglycan Mixture, Sulodexide, and a Chemically Modified Heparin Derivative, Suleparoide", Sem. Thromb. Hemost. 19 (Suppl. 1):49-57 (1993).

Caulfield J.P. et al., "Loss of Anionic Sites from the Glomerular Basement Membrane in Aminonucleoside Nephrosis", Lab. Invest. 39:505-512 (1978).

Cospite M. et al., "Haemodynamic Effects of Sulodexide in Post-Thrombophlebitic Syndromes", Acta Therapeutica 18:149-159 (1992).

Crepaldi G. et al., "Double-Blind Multicenter Trial on a New Medium Molecular Weight Glycosaminoglycan. Current Therapeutic Effects and Perspectives for Clinical Use", Atherosclerosis 81:233-243 (1990).

Dedov I. et al., "A Randomized, Controlled Study of Sulodexide Therapy for the Treatment of Diabetic Nephropathy", Nephrol. Dial. Transplant 12:2295-2300 (1997).

Diamond J.R. and Karnovsky M., "Nonanticoagulant Protective Effect of Heparin in Chronic Aminonucleotide Nephrosis", Renal Physiol. 9:366-374 (1986).

(Continued)

Primary Examiner—Patrick Lewis
(74) Attorney, Agent, or Firm—Jones Day

(57) ABSTRACT

The present invention provides oral formulations of Sulodexide for the treatment of diabetic nephropathy in patients with both insulin dependent and non-insulin dependent diabetes mellitus. Oral formulations containing doses adapted for administration to obtain a reduction in albumin excretion in patients with both micro and macro albuminuria and to produce lasting improvement in albumin excretion rate are provided. Methods of treating diabetic nephropathy using these formulations are also provided.

4 Claims, 1 Drawing Sheet

OTHER PUBLICATIONS

Figure 1:
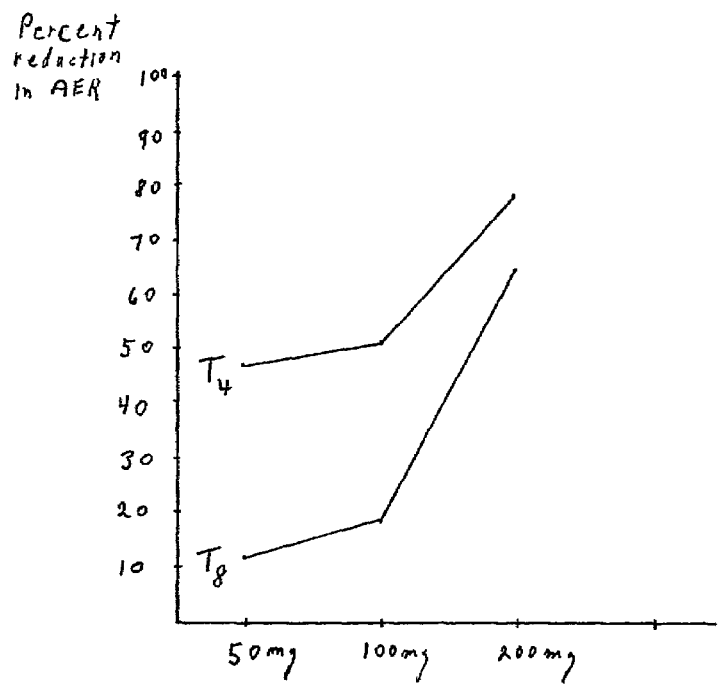

Ebert, "Soft Elastic Gelatin Capsule", Pharm. Tech, 1(5):44-50 (1977).

Gambaro G. and Van Der Woude J., "Glycosaminoglycans: Use in Treatment of Diabetic Nephropathy", Am. Soc. Nephrol. 11:359-368 (2000).

Gambaro G. et al., "Glycosaminoglycans Prevent Morphological Renal Alterations and Albuminuria in Diabetic Rats", Kidney Int. 42:285-291 (1992).

Goldman L. and Claude Bennett J (editors), Cecil Textbook of Medicine (pp. 1281-1283), 21st Edition (2000), W.B. Saunders, Philadelphia.

Groggel G.C. et al., "Changes in Heparin Sulfate Correlate with Increased Glomerular Permeability", Kidney Int. 33:517-523 (1988).

Harenberg J, "Review of Pharmacodynamics, Pharmacokinetics, and Therapeutic Properties of Sulodexide",Medicinal Research Rev. 18:1-20 (1998).

Kanwar Y.S. et al., "Basement Membrane Proteoglycans of the Kidney", Sem. Nephrol. 5:307-313 (1985).

Parthasarathy N. and Spiro, R., "Effect of Diabetes on the Glycosaminoglycan Component of the Human Glomerular Basement Membrane", Diabetes 31:738-741 (1982).

Poplawska A. et al., "Effect of Glycosaminoglycans on Urinary Albumin Excretion in Insulin-Dependent Diabetic Patients with Micro- or Macroalbuminuria", Diabetes Res Clin. Pract. 38:109-114 (1997).

Purkerson, M. et al., "N-Desulfated/Acetylated Heparin Ameliorates the Progression of Renal Disease in Rats with Subtotal Renal Ablation", J. Clin. Invest. 81:69-74 (1988).

Radhakrishnamurthy B. et al., "Studies of Glycosaminoglycan Composition and Biologic Activity of Vessel®, a Hypolipidemic Agent", Atherosclerosis 31:217-229 (1978).

Remington's Pharmaceutical Sciences, 1995, Mack Publ. Co., Easton, PA. (Table of Contents).

Salvetti A. et al., "Renal Protection and Antihypertensive Drugs", Drugs 57:665-693 (1999).

Škrha J. et al., "Glycosaminoglycan Sulodexide Decreases Albuminuria in Diabetic Patients", Diabetes Res. Clin. Pract. 38:25-51 (1997).

Solini A. et al., "Therapy with Glycosaminoglycans Lowers Albumin Excretion Rate in Non-Insulin Dependent Diabetic Patients with Macroalbuminuria", Diabetes Nutr. Metab. 7:304-307 (1994).

Sozzi C., "The Preventive Activity of an Extractive Glycosaminoglycane (Sulodexide) in Relapses of TIA. A Short Term Study", Eur. Rev. Med. Pharmacol. Sci. 6:295-300 (1984).

Szelanowska M. et al., "A Pilot Study of the Effect of the Glycosaminoglycan Sulodexide on Microalbuminuria in Type I Diabetic Patients", Curr. Med. Res. Opin. 13:539-545 (1997).

Thomas D.P. et al., "Relative Efficacy of Heparin and Related Glycosaminoglycans as Antithrombic Drugs", Ann. N.Y. Acad. Sci. 556:313-322 (1989).

Shin, J. of the Med. Soc. of Toho Univ. vol. 38, No. 3, pp. 374-382 (1991).

Mogami, J. of the Jap. Diabetes Soc., (Abstract, p. 111) vol. 34, No. 2, pp. 105-111 (1991).

Shin et al., Current Status of Prev. and Treat. of Diabetic complications, pp. 567-569 (1990).

Kaizu et al., J. of Diabetic Complications, vol. 5, Nos. 2-3, pp. 92-94 (1991).

Gaddi et al., 1996, "Meta Analyisi of Some Results of Clinical Trials on Sulodexide Therapy in Peripheral Occlusive Arterial Disease", J. of Int. Med. Res. 24:389-406.

International Search Report, PCT International Application No. PCT/US01/18411, filed Jun. 6, 2001.

Nielsen et al., 1999, "Transcapillary escape rate and albuminaria in Type II diabetes. Effect of short term treatement with low molecular weight heparin", Diabetologia 42:60-67.

Solini et al., 1997, "Glycosaminoglycans Delay the Progression of Nephropathy in NIDDM", Diabetes Care 20:819-823.

Sorrenti et al., 1997, "Glycosaminoglycans as a Possible Tool for Micro and Macroalbuminuria in Diabetic Patients", J. of Int. Med. Res. 25:81-86.

Harenberg, 1998, Review of Pharmacodynamics, Pharmacokinetics, and Therapeutic Properties of Sulodexide, pp. 1-20, John Wiley & Sons, Inc., pub.

Messa et al., 1995, Pharmacodynamic Effects of Sulodexide on Profibrinolytic and Haemorrheological Patterns, Clin. Drug Invest. 10(3):165-171.

Saviano et al., 1993, Double-blind, double-dummy, randomized, multi-centre clinical assessment of the efficacy, tolerability and dose-effect relationship of sulodexide in chronic venous insufficiency, Curr. Med. Res. Opin. 13:96-108.

* cited by examiner

Percent reductions in albumin excretion rate (AER) in DM2 patients (Micro and Macroalbuminuric patients combined Dose regimen of Sulodexide per day
$T_4$ = end of Treatment period
$T_8$ = end of 4 month post treatment follow up period

METHODS AND COMPOSITIONS USING SULODEXIDE FOR THE TREATMENT OF DIABETIC NEPHROPATHY

This non-provisional application claims the priority benefit of U.S. Provisional Application No. 60/209,907, which was filed on Jun. 7, 2000.

FIELD OF THE INVENTION

The present invention relates to pharmaceutical compositions comprising Sulodexide in specific dosages and methods of using specific dosages of Sulodexide for the treatment of patients with diabetic nephropathy and albuminuria caused by, for example, insulin dependent or non-insulin dependent Diabetes Mellitus.

BACKGROUND OF THE INVENTION

The use of glycosaminoglycans, such as heparin, in various anticoagulant and antithrombotic therapies is well known. Sulodexide is a glycosaminoglycan of natural origin extracted from mammalian intestinal mucosa that posses an anticoagulant activity. Sulodexide has a sulfation degree lower than those of heparin, as shown by Radhakrishnamurthy B. et al., Atherosclerosis, 31, 217-229 (1978). The preparation of Sulodexide is described in U.S. Pat. No. 3,936,351, (incorporated herein by reference in its entirety).

Sulodexide is marketed in Europe under the trademark VESSEL DUE F(R) and is prescribed for the treatment of vascular pathologies with thrombotic risk such as peripheral occlusive arterial disease (POAD), healing of venous leg ulcers and intermittent claudication (See Harenberg J, Med. Res. Rev. vol. 18,1-20 (1998), Crepaldi G. et al., Atherosclerosis, 81, 233, (1990)), cardiovasculopathies, as described by Tramarin R. et al. Medical Praxis, 8, 1, (1987), cerebrovasculopathies as described by Sozzi C., Eur. Rev. Med. Pharmacol Sci. 6, 295, (1984) and venous pathologies of the lower limbs, as described by Cospite M. et al, Acta Therapeutica, 18, 149, (1992).

Diabetic nephropathy is a common and serious complication of the disease Diabetes Mellitus and is the leading cause of chronic renal failure (CRF) in the U.S., being responsible for one third of all CFR cases. The precise cause of the changes produced by diabetes in the kidney are not all known. However, it is known that a hallmark of diabetic nephropathy is the presence of protein in the urine (proteinuria) of patients. The protein albumin, which is normally present in plasma, is excreted in the urine of patients with diabetic nephropathy. This is referred to as albuminuria. The rate of excretion of this protein is a good indicator of the extent of the renal pathology. High levels of albumin excretion strongly predict accelerated diminution in glomerular filtration rate (GFR) and eventual renal failure. The degree of albumin excretion is used to divide patients into two groups; those with microalbuminuria (excretion of 200 mcg/min or less), and those with macroalbuminuria (excretion of more than 200 mcg/min).

The antihypertension drugs known as ACE inhibitors (ACEI) decrease albuminuria in diabetic nephropathy but the pathological changes in the kidney and renal functional deterioration may continue toward end stage renal disease (ESRD). ACEI are also less effective in type 2 or non-insulin dependent diabetic (DM2) nephropathy as compared to that seen in type 1 or insulin dependent diabetes (DM1). Salvetti A. et al. Drugs 57(5):665-693 (1999).

Diabetic nephropathy is a clinically well defined pathological condition characterized by proteinuria, hypertension, edema and renal insufficiency and generally occurs in patients suffering from diabetes for more than ten years. Diabetic nephropathy causes a number of structural changes in the kidney, the most characteristic of which is the glomerular injury detectable by the enlargement of the mesangium and by the thickening of the basement membrane in the glomerulus. (See Cecil Textbook of Medicine (pages 1281-1283), Edited by Goldman L. and Claude Bennett J., $21^{st}$ Edition (2000), W. B. Saunders, Philadelphia).

Glycosaminoglycans such as Sulodexide are known to decrease albumin excretion in patients with diabetic nephropathy. The precise mechanism is not known but may include the following:

1) Restoration of the physiologic glomerular membrane anionic charge barrier via enhanced synthesis and sulfation of heparan sulfate in renal vascular membranes, and direct replenishment of renal heparan sulfate,
2) Inhibition of Transforming Growth Factor beta-1 (TGF beta-1) mediated mesangial matrix overproduction,
3) Inhibition of endothelin mediated tubulo-interstitial fibrosis, and
4) Inhibition of mesangial cell hyperplasia.

(See Harenberg J., Med. Res. Rev. vol. 18, 1-20 (1998), Gambaro G. and Van Der Woude, J. Am. Soc. Nephrol. 11:359-368 (2000)).

Kanwar Y. S. et al., Sem. Nephrol., 5, 307, (1985) and Groggel G. C. et al., Kidney Int., 33, 517, (1988), have produced evidence of the probable role of glycosaminoglycans in helping the integrity and the functioning of the renal cells.

Moreover, Canfield J. P. et al., Lab. Invest., 39, 505, (1978), previously showed a decrease of glycosaminoglycans in the glomerular basement membrane in many conditions of nephropathy, while Baggio B. et al., Nephron., 43, 187, (1986) showed an increased urinary elimination of glycosaminoglycans in diabetic, non-albuminuric, patients. This increased excretion of glycosaminoglycans in diabetic nephropathies was shown also by Partasarathy N. et al., Diabetes, 31, 738, (1982).

In addition, Diamond J. R. et al., Renal Physiol., 9, 366, (1986) and Parkerson M. B. et al., J. Clin. Invest., 81, 69, (1988), showed in animals the potential protective effect of heparin and its derivatives in models of experimental nephropathy not related to diabetic nephropathy, like chronic nephrosis from aminoglycosides and renal pathologies resulting from the subtotal renal ablation in the rat.

The use of heparin, low molecular weight heparin fractions, chemically modified heparins or low molecular weight dermatan sulfate in the treatment of both diabetic nephropathy and neuropathy has been investigated in the European Patent Publication EP 0513513 and U.S. Pat. No. 5,236,910 (incorporated herein by reference in its entirety). The possibility of therapeutic use was shown by means of pharmacological tests in animals: diabetes was caused by streptozotocin in Sprague Dawley male albino rats and the diabetic rats were treated with the above mentioned glycosaminoglycans. The effectiveness of treatment in animals was determined on the basis of the diminution of albuminuria and of the reduction of the thickness of the basal glomerular membrane and the increase of the glomerular anionic charges.

The use of Sulodexide to treat diabetic nephropathy is described in U.S. Pat. No. 5,496,807 (incorporated herein by reference in its entirety). This patent describes the effectiveness of Sulodexide in two clinical studies in which diabetic patients, some with microalbuminuria and some with macroalbuminuria, were given doses of Sulodexide. In one study Sulodexide was administered at the then recognized safe and effective dose of 1000 lipoproteinlipase releasing units/day (LRU's/day) (equivalent to 100 mg/day). This daily dose required two 250 LRU capsules of VESSEL DUE F(R) administrated twice a day. After 60 days, 8 out of 10 diabetic patients, 4 with microalbuminuria and 4 with macroalbuminuria showed an average decrease of 44% and 35% in albumin excretion respectively. Two of the patients with microalbuminia did not get any improvement. In addition, no substantial change in the glomerular filtration rate of any of the patients was noted at follow-up four months after the end of treatment.

The second clinical trial described in U.S. Pat. No. 5,496,807 involved three microalbuminuric and two macroalbuminuric diabetic patients administered 600 LRU/day of Sulodexide by intramuscular route for 21 days. All five of these patients showed a significant lowering of albumin excretion.

In neither of these studies, disclosed in the '807 patent, was the improvement in albumin excretion shown to be maintained after the Sulodexide administration ended. The dose range disclosed in this patent specification and the claims was 500 to 1500 L.R.U.'s or 50 to 150 mg./day.

Recently, the use of glycosaminoglycans, including Sulodexide, in the treatment of diabetic nephropathy has been reviewed by Gambaro G. and Van Der Woude in *J. Am. Soc. Nephrol.* 11: 359-368 (2000). In this review Sulodexide is described as being active in preventing diabetic nephropathy in an experimental animal model, Gambaro et al. *Kidney Int.* 42: 285-291, 1992. In addition, Sulodexide is said to have been shown to reduce albuminuria in both insulin dependent diabetes mellitus (IDDM) and non-insulin dependent diabetes mellitus (NIDDM). (See Skrha J. et al. *Diabetes Res. Clin. Pract.* 38: 25-51 (1997), Solini A. et al. *Diabetes Nutr. Metab.* 7: 304-307, (1994), Poplawska A. et al. *Diabetes Res Clin. Pract.* 38: 109-114, (1997), Dedov. I. et al. *Nephrol Dial Transplant* 12:2295-2300, (1997) and Szelanowska M. et al. *Curr Med. Res. Opin.* 13:539-545, (1997)).

In these studies Sulodexide treatment in IDDM was found to be consistently effective in reducing microalbuminuria. However this hypoalbuminuric effect was observed in only 30 to 50% of NIDDM patient, and at most the effect lasted only several weeks after the withdrawal of the Sulodexide. In the studies reviewed by Gambaro the maximum dose of Sulodexide used was 100 mg/day orally and more typically doses of only 60 mg/day were used either by the oral route or by intra muscular injection. Previous experience in using Sulodexide to treat other pathological conditions had shown that doses of 25-100 mg/day (250-1000 LRU's) were considered clinically effective.

In addition, another reason for the use of such low doses was the concern over possible risks and side effects of a drug such as Sulodexide. For example Sulodexide is known to have antithrombotic activity equal to that of heparin, Thomas D. P. et al. *Ann. N.Y. Acad. Sci.*, 556, 313 (1989) and to completely prevent clot formation at high doses. In primates the oral administration of 10 mg/kg of Sulodexide increased tissue plasminogen activator (TPA) from 5 to 10 ng/ml and produced an increase of U-PA from 3 to 6.5 ng/ml. This suggests that Sulodexide is a strong anticoagulant, antithrombotic and profibromolytic agent. Callas D. D. et al., *Thromb. Hemost.,* 19 (Suppl. 1), 49 (1993).

Effective oral doses of Sulodexide have been in the range of 25-100 mg/day or 250-1000 LRU/day for the treatment of vascular pathologies Harenberg J., *Med. Res. Rev.* vol. 18, 1-20 (1998). The largest dose reported in the literature to our knowledge for the treatment of diabetic nephropathy was an oral dose of 1000 LRU/day or 100 mg/day. This dose did decrease the rate of albumin excretion in patients with NIDDM (type II diabetes or DM2) but the albumin excretion rate was found again increased four months after cessation of treatment Solina A. *Diab. Nutr. Metabo.,* 7, 304 (1994).

The art concerning the use of Sulodexide to treat vascular conditions teaches that doses of 100 mg/day or 1000 LRU's or less are effective and that higher doses may produce unwanted or dangerous heparin like effects. However, doses in the range of 100 mg./day (1000 LRU's) or less, have not proved effective in all subjects with diabetic nephropathy and have not been shown to produce lasting improvement in the albumin excretion rate in treated patients. (See Harenberg J. *Med. Res. Rev.* vol. 18, 1-20 (1998) and Gambaro G. and Van Der Woude, *J. Am. Soc. Nephrol.* 11:359-368 (2000)). Furthermore, oral administration is much more desirable and less problematic to the patient as compared to intramucular administration.

For these reasons there is a need for oral formulations of Sulodexide in dosage formulations adapted to adequately treat diabetic nephropathy in both macro and micro albuminic patients and to produce lasting improvement in albumin excretion rate in diabetic patients.

SUMMARY OF THE INVENTION

The present invention is directed to pharmaceutical compositions of Sulodexide in unit dosages particularly well suited for the treatment of diabetic nephropathies. These pharmaceutical compositions or formulations comprise effective and non-toxic amounts of Sulodexide or a pharmaceutically acceptable salt thereof within the range from about 100 mg. (1000 LRU) to about 1000 mg. (10,000 LRU); and a pharmaceutically acceptable carrier, diluent or excipient.

The compositions are preferably pharmaceutical preparations suitable for oral administration, comprising an amount of Sulodexide sufficient to produce a substantial reduction in the albumin excretion rate (AER) in patients with diabetic nephropathy who have micro or macro albuminuria as a result of diabetes induced changes in renal functioning, together with a pharmaceutical excipient, diluent, or carrier.

The present invention encompasses single unit dosage forms comprising an amount of Sulodexide sufficient to produce an immediate and lasting reduction in AER without significant adverse side effects.

In addition, this invention encompasses methods of treating patients with diabetic nephropathy using these specific dosage formulations.

The doses of Sulodexide disclosed in the present invention are novel in the treatment of diabetic nephropathy and are based, at least in part, on the discovery that such doses produce lasting improvement in albumin excretion rate and do not produce the expected toxic effects.

These and other features, aspects and advantages of the present invention will become better understood with reference to the following description, FIGURE and appended claims.

BRIEF DESCRIPTIONS OF THE DRAWINGS

FIG. 1 shows the percent albumin excretion rate (AER) reduction in DM2 patients (micro and macro albuminuric patients combined).

DETAILED DESCRIPTION OF THE INVENTION

The present invention encompasses pharmaceutical compositions for the treatment of a human suffering from diabetic nephropathy with micro or macro albuminuria which encompasses an amount of Sulodexide, preferably in orally administratable form, said amount of Sulodexide being sufficient to significantly decrease the amount of albumin excreted in the urine of a patient with diabetic nephropathy.

Sulodexide is available commercially under the trademark VESSEL DUE F(r), and it can be made by the methods disclosed in U.S. Pat. No. 3,936,351.

This invention is based in part on the discovery of unexpected benefits of using doses of Sulodexide in humans much higher than previously used, including the absence of expected adverse side effects at the higher dose levels. The unexpected benefits of the higher doses are demonstrated in patients given oral Sulodexide for the treatment of diabetic nephropathy.

The effectiveness of these higher doses is unexpected because in the treatment of conditions other than diabetic nephropathy much lower doses of Sulodexide have been used and found clinically effective. Even in the treatment of diabetic nephropathy doses of Sulodexide larger than 100 mg/day or 1000 LRU's have never been reported and to our knowledge the art does not teach that higher doses would be effective and non-toxic. In addition, the possibility of adverse heparin like side effects was well known and this constituted teaching away from the use of these higher doses of Sulodexide.

The present invention encompasses a method for treating diabetic nephropathy in a human which comprises administering to said human an amount of Sulodexide or a pharmaceutically acceptable salt thereof, of from about 100 mg. (1000 LRU) to 1000 mg. (10,000 LRU) in a solid unit dosage form, said amount being administered one or more times per day and said amount being sufficient to reduce the albumin excretion rate but insufficient to cause adverse side effects. In addition, the present invention encompasses unit dose forms of Sulodexide of about; 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, and 1000 mg.

The therapeutic effectiveness of Sulodexide at high doses has been evaluated in a placebo controlled double-blind study. The results of this study reported in the example show below compared placebo treatment with 200 mg/day of Sulodexide and showed a 70% reduction in AER in patients with IDDM (DM1) and 77% reduction in AER in patients with NIDDM (DM2) compared to a 48% reduction and 52% in patients treated with a 100 mg/day dose for four months. Even more dramatic was the improvement in albumin excretion rate shown at follow-up, four months post treatment. In this follow up portion of the study the 200 mg/day dose produced a 62% reduction in AER in DM1 patients and a 63% reduction in AER in DM2 patient compared to 38% and 18% reductions respectively in patients receiving 100 mg/day.

Thus, patients with DM2 receiving 200 mg/day of Sulodexide showed more than three times the reduction in albumin excretion at a point four months post treatment as compared to the patients receiving 100 mg/day. This dramatic non-linear effect of high dose Sulodexide was highly significant clinically and unexpected.

The following example is given to illustrate the invention and cannot be taken on a limitation of the invention itself.

EXAMPLE

Oral Treatment of Albuminuria in Nephropathic Diabetic Patients with Sulodexide The objective of this study was to evaluate the efficacy of three dose regimens of oral Sulodexide versus placebo, in both DM1 and DM2 patients with diabetic nephropathy and albuminuria.

The experimental methodology was to randomly divide 240 patients with diabetic nephropathy and albuminuria into four groups. These groups received treatment with placebo or with oral Sulodexide at doses of 50, 100 or 200 mg per day. The active treatment phase was four months long and this was followed by an additional post treatment follow up after four months. The assignment and treatment of the patients was done in a double blind fashion.

Inclusion criteria for the study required a stable blood pressure of less than 160/90, a serum creatinine of less than 150 μmol/L, proteinuria of less than 3 g/day and stable HgBA1C.

The primary end point changes in albumin excretion rate (AER) were determined by three overnight urine collections (analysis by ANCOVA adjusting for the baseline value of log AER).

The results demonstrated that the percent reduction in AER after 4 months treatment with Sulodexide was significantly different from placebo, and approximately linear to dose increments. The group receiving Sulodexide at 50 mg/day had a 31% reduction in AER (p=0.0026), the 100 mg/day group, a 50% reduction (p=0.0001), and the 200 mg/day group a 75% reduction (p=0.0001). After 4 months follow-up, the Sulodexide 100 mg group maintained a 28% AER reduction compared to placebo (p=0.0179), and the 200 mg group maintained a 65% reduction (p=0.0001). Sub-analysis by type of diabetes (DM1 vs. DM2), micro vs. macroalbuminuria, and patients treated with or without ACE inhibitors demonstrated similar reductions in AER. Sulodexide at all dose levels was well tolerated. There were no significant changes in hemotologic, coagulation, and liver function parameters among the four groups. No deaths were recorded.

The conclusions were that oral Sulodexide reduces AER in patients with diabetic nephropathy caused by both DM1 and DM2 who are demonstrating micro or macroalbuminuria. The study showed no evidence of a plateau effect with the maximum doses used in this study. This was very significant and unexpected because the maximum dose used in this study was twice the maximum dose of Sulodexide used in any prior studies.

In addition, the ability of oral Sulodexide to reduce albuminuria persisted following a four month cessation of treatment. This effect was a dramatic and unexpected finding and demonstrated a lasting beneficial effect of Sulodexide at high doses. This may be due to replenishment of the glomerular membrane electrostatic charge barrier or some other ability of high dose Sulodexide to produce a "healing" effect.

The additional efficacy of high dose Sulodexide was observed even in diabetic nephropathy patients already taking ACE inhibitors.

These findings show the ability of Sulodexide to lower albuminuria in nephropathic diabetic patients on a long term basis, beyond improvements achieved with ACE inhibitors. This may be of particular important in NIDDM or DM2 nephropathic patients, who respond less well to ACE inhibitors and who compromise the fastest growing group of patients with ESRD.

The clinical results showing the effectiveness of treatment with various doses of Sulodexide are summarized in the following table;

TABLE 1

Percent AER Reduction by Patient Subgroups

| Group | DM1 | | DM2 | | Microalbuminuria | | Macroalbuminuria | | ACEI Therapy | | | |
|---|---|---|---|---|---|---|---|---|---|---|---|---|
| | | | | | | | | | Yes | | No | |
| | T4 | T8 | T4 | T8 | T4 | T8 | T4 | T8 | T4 | T8 | T4 | T8 |
| Sulodexide 50 mg | 16% | 0% | 47% | 12% | 30% | 0% | 35%* | 20% | 35%* | 12% | 27% | −5% |
| Sulodexide 100 mg | 48%* | 38% | 52%* | 18% | 50%* | 25% | 49%* | 42%* | 51%* | 28% | 48%* | 36% |
| Sulodexide 200 mg | 70%* | 62%* | 77%* | 63%* | 74%* | 65%* | 75%* | 62%* | 74%* | 60%* | 74%* | 67%* |

T4 = end of treatment period
T8 = end of 4 month post treatment follow up period
*denotes p-value < 0.05
**denotes p-value < 0.01
ACEI Therapy denotes simultaneous treatment with angiotensin converting enzyme inhibitors The pharmaceutical compositions of the present invention comprise Sulodexide as the active ingredient, and may also contain a pharmaceutically acceptable carrier, excipient or diluent and optionally other therapeutic ingredients.

Any formulation suitable for oral administration may be used in the present invention. These dosage forms include tablets, coated tablets, caplets, hard gelatin capsules, soft gelatin capsules, troches, dragées, dispersions, suspensions, solutions, patches and the like, including sustained release formulations well known in the art. See, e.g., *Introduction to Pharmaceutical Dosage Forms,* 1985, Ansel, H. C., Lea and Febiger, Philadelphia, Pa.; *Remington's Pharmaceutical Sciences,* 1995, Mack Publ. Co., Easton, Pa.

In practical use, the active agent (Sulodexide) in the pharmaceutical compositions of the invention can be combined as the active ingredient in intimate admixture with a pharmaceutically acceptable carrier according to conventional pharmaceutical compounding techniques. The carrier may take a wide variety of forms and comprises a number of components depending on the form of preparation desired for administration. The compositions of the present invention include, but are not limited to, suspensions, solutions and elixirs; aerosols; or excipients, including, but not limited to, starches, sugars, microcrystalline cellulose, diluents, granulating agents, lubricants, binders, disintegrating agents, and the like.

Preferably, the pharmaceutical composition is in the form of an oral preparation. Because of their ease of administration, tablets and capsules are preferred and represent the most advantageous oral dosage unit form, in which case solid pharmaceutical excipients are employed. If desired, tablets may be coated by standard aqueous or nonaqueous techniques.

Preferably, the oral pharmaceutical compositions of the present invention may be administered in single or divided doses, from one to four times a day. The oral dosage forms may be conveniently presented in unit dosage forms and prepared by any methods well known in the art of pharmacy.

Pharmaceutical compositions of the present invention suitable for oral administration may be presented as discrete pharmaceutical unit dosage forms, such as capsules, cachets, soft elastic gelatin capsules, tablets, caplets, or aerosols sprays, each containing a predetermined amount of the active ingredients, as a powder or granules, or as a solution or a suspension in an aqueous liquid, a non-aqueous liquid, an oil-in-water emulsion, or a water-in-oil liquid emulsion.

Such compositions may be prepared by any methods well known in the art of pharmacy, but all methods include the step of bringing into association one or more active ingredient(s) with the carrier. In general, the compositions are prepared by uniformly and intimately admixing the active ingredients with liquid carriers or finely divided solid carriers or both, and then, if necessary, shaping the product into the desired presentation. Oral solid preparations are preferred over oral liquid preparations. One preferred oral solid preparation is tablets, but the most preferred oral solid preparation is capsules.

For example, a tablet may be prepared by compression or molding, optionally, with one or more accessory ingredients. Compressed tablets may be prepared by compressing in a suitable machine the active ingredient in a free-flowing form, such as powder or granules, optionally mixed with a binder, lubricant, inert diluent, granulating agent, surface active or dispersing agent, or the like. Molded tablets may be made by molding, in a suitable machine, a mixture of the powdered compound moistened with an inert liquid diluent. Preferably, each tablet, cachet, caplet, or capsule contains from about 100 mg to about 1000 mg of Sulodexide, more preferably from about 100 mg to about 250 mg Sulodexide.

Pharmaceutical compositions of the present invention suitable for oral administration may be formulated as a pharmaceutical composition in a soft elastic gelatin capsule unit dosage form by using conventional methods well known in the art. See, e.g., Ebert, *Pharm. Tech,* 1(5):44-50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain a preservative, such as methyl- and propylparabens and sorbic acid, to prevent the growth of fungi. The active ingredient may be dissolved or suspended in a liquid vehicle or carrier, such as vegetable or mineral oils, glycols, such as polyethylene glycol and propylene glycol, triglycerides, surfactants, such as polysorbates, or a combination thereof.

In addition to the common dosage forms set out above, the compounds of the present invention may also be administered by controlled release means or delivery devices that are well known to those of ordinary skill in the art, such as those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, the disclosures of which are each incorporated herein by express reference thereto.

These pharmaceutical compositions can be used to provide slow or controlled-release of one or more of the active ingredients therein using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable controlled-release formulations known to those of ordinary skill in the art, including those described herein, may be readily selected for use with the pharmaceutical compositions of the invention. Thus, single unit dosage forms suitable for oral administration, such as tablets, capsules, gelcaps, caplets, and the like, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; and 3) increased patient compliance.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

The controlled-release of an active ingredient may be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, microspheres, or the like, or a combination thereof, that facilitates the controlled-release of the active ingredient.

Pharmaceutical stabilizers may also be used to stabilize compositions containing Sulodexide; acceptable stabilizers include but are not limited to L-cysteine hydrochloride, glycine hydrochloride, malic acid, sodium metabisulfite, citric acid, tartaric acid and L-cysteine dihydrochloride.

All references to the literature and all patents mentioned in this specification are incorporated herein by reference in their entirety.

The present invention is not to be limited in terms of the particular embodiments described in this application, which are intended as single illustrations of individual aspects of the invention. Functionally equivalent pharmaceutical compositions and methods of treatment within the scope of the invention, in addition to those enumerated herein, will be apparent to those skilled in the art from the foregoing description. Such modifications and variations are intended to fall within the scope of the appended claims.

We claim:

1. A method of treating a patient with diabetic nephropathy comprising orally administering to a human in need of treatment from diabetic nephropathy, an amount of Sulodexide, or a pharmaceutically acceptable salt thereof, at a dose of about 200 mg/day, said amount being sufficient to decrease albumin excretion rate without causing adverse side effects.

2. The method of claim 1 wherein Sulodexide is administered orally as a tablet, a capsule or a liquid suspension.

3. The method of claim 1 wherein the Sulodexide is administered in one to four unit doses per day.

4. The method of claim 1 wherein Sulodexide or salt thereof is administered orally as a tablet, coated tablet, caplet, hard gelatin capsule, soft gelatin capsule, troche, dragee, dispersion, suspension or solution.

* * * * *